United States Patent [19]

Pennington

[11] Patent Number: 4,785,134
[45] Date of Patent: Nov. 15, 1988

[54] ALLYL ALCOHOL PRODUCTION USING MOLTEN NITRATE SALT CATALYSTS

[75] Inventor: B. Timothy Pennington, Sulphur, La.

[73] Assignee: Olin Corporation, Cheshire, Conn.

[21] Appl. No.: 149,259

[22] Filed: Jan. 28, 1988

[51] Int. Cl.[4] .................... C07C 29/48; C07C 29/50; C07C 33/03
[52] U.S. Cl. ................................. 568/910.5; 568/910
[58] Field of Search ............................ 568/910, 910.5

[56] References Cited

U.S. PATENT DOCUMENTS

| | | | |
|---|---|---|---|
| 2,190,453 | 2/1940 | King et al. | 568/910.5 |
| 2,609,401 | 9/1952 | Hess et al. | 568/910 |
| 3,284,494 | 11/1966 | Schoenbrunn | 568/910 |
| 3,415,885 | 12/1968 | Hooper | 568/910 |
| 3,462,494 | 8/1969 | Blackley | 568/910 |
| 3,993,672 | 11/1976 | Arzoumanian et al. | 568/910 |
| 4,064,175 | 12/1977 | McMahon | 568/910 |

FOREIGN PATENT DOCUMENTS

| | | | |
|---|---|---|---|
| 552812 | 2/1958 | Canada | 568/910 |
| 577992 | 6/1946 | United Kingdom | 568/910 |

OTHER PUBLICATIONS

Kirk-Othmer's "Encyclopedia of Chemical Technology", 3rd Edition, vol. 2, Alkoxides, Metal and Antibiotics (Peptides), p. 103 (1978).

Primary Examiner—J. E. Evans
Attorney, Agent, or Firm—Dale Lynn Carlson

[57] ABSTRACT

A novel process for producing allyl alcohol and, more specifically, to a process which utilizes a molten nitrate salt catalyst.

16 Claims, No Drawings

ALLYL ALCOHOL PRODUCTION USING MOLTEN NITRATE SALT CATALYSTS

FIELD OF THE INVENTION

This invention relates generally to a novel process for producing allyl alcohol and, more specifically, to a process which utilizes a molten nitrate salt catalyst.

BACKGROUND OF THE INVENTION

Allyl alcohol is a widely used reactant in the production of glycerol as well as other organic chemicals (e.g., 1,4-butanediol). Conventional processes for the manufacture of allyl alcohol typically involve one of the following: (a) the alkaline hydrolysis of allyl chloride, (b) the oxidation of propylene to acrolein, followed by the reaction of the acrolein with a secondary alcohol to form allyl alcohol and a ketone, or (c) isomerization of propylene oxide using a lithium phosphate catalyst. None of these methods offer a direct one-step synthesis of allyl alcohol.

New methods of producing allyl alcohol that provide advantageous selectivity in a simple, inexpensive production process would be highly desirable.

SUMMARY OF THE INVENTION

In one aspect, the present invention relates to a process for producing allyl alcohol by reacting propylene with an oxygen-containing gas in the presence of at least one molten nitrate salt catalyst. The process preferably is effected under reaction conditions which provide a molar selectivity to allyl alcohol of at least about 40 percent based upon the propylene reactant.

In another aspect, the present invention relates to a process for producing allyl alcohol from propylene, or mixtures of propylene and propane, which comprises bubbling an oxygen-containing gas and said propylene or mixture through a bath of at least one molten nitrate salt catalyst under reaction conditions which include a temperature of between about 135° C. and about 600° C. (preferably between about 135° C. and about 350° C.) and a superatmospheric pressure not exceeding 100 atmospheres (preferably up to about 40 atmospheres).

In still another aspect, the present invention relates to a process for producing allyl alcohol by reacting propylene with an oxygen-containing gas in the presence of a catalyst, said catalyst consisting essentially of a mixture of sodium nitrate and potassium nitrate containing between about 20 weight percent and about 80 weight percent of sodium nitrate based upon the total amount of sodium nitrate and potassium nitrate in said mixture, under reaction conditions which include a reaction temperature of between about 275° C. and about 350° C. and a reaction pressure of between about 100 psig and about 400 psig.

In yet another aspect, the present invention relates to a process for producing allyl alcohol by reacting propylene with an oxygen-containing gas in the presence of a catalyst, said catalyst consisting essentially of a mixture of sodium nitrate, potassium nitrate and lithium nitrate, containing between about 10 weight percent and about 30 weight percent of lithium nitrate and between about 15 weight percent and about 75 weight percent of sodium nitrate based upon the total amount of said mixture, under reaction conditions which include a reaction temperature of between about 200° C. and about 350° C. and a reaction pressure of between about 100 psig and about 400 psig.

DETAILED DESCRIPTION OF THE INVENTION

It has now been found in accordance with the present invention that allyl alcohol is produced by the reaction of propylene with an oxygen-containing gas in the presence of at least one molten nitrate salt. Further, it has now been surprisingly discovered that high molar selectivities to allyl alcohol of at least about 40 percent are provided by suitable selection of reaction conditions.

Several factors will affect the reactant conversion to allyl alcohol and the selectivity of allyl alcohol production vis-a-vis by-product production in accordance with the process of the present invention. These factors include, for example: the contact time of the molten salt with the oxygen-containing gas, the temperature of the reactor product gases, the molten salt temperature, the molten salt composition, the feed gas temperature, the feed gas composition, and the feed gas pressure.

The oxygen-containing gas useful as a reactant in the present invention can be any such gas. Typically, air is employed as the oxygen-containing gas based upon its ready availability. However, other oxygen-containing gases such as pure oxygen may be employed, if desired, and the use of oxygen is expected to be preferred in a commercial setting.

The propylene reactant useful in the present invention is suitably propylene itself or a mixture of propylene and propane, and the choice is typically based upon commercial availability.

The propylene is preferably preheated to prevent condensation in the line delivering this gas to the reactor. Alternatively, both the oxygen-containing gas and the propylene (collectively referred to herein as "the feed gases") can be preheated to prevent condensation at any point in the feed gas system. However, in the absence of preheat, the molten nitrate salt will rapidly heat the feed gases up to reaction temperature. If the feed gas is preheated, it preferably is maintained at at least about 100° C. in the feed gas line(s).

The molten nitrate salt(s) is generally maintained at a temperature sufficient to keep the salt(s) in a molten condition. Generally, the temperature is maintained between about 135° C. (275° F.) and about 600° C. (1,000° F.) during the reaction in accordance with the present invention. The specific temperature selected is based upon the melting point of the particular molten nitrate salt chosen.

The molten salt(s), in addition to functioning as a catalyst, also serve as a temperature regulator. More specifically, the molten nitrate salt(s) have a high heat absorption capacity, enabling them to absorb large quantities of heat during the exothermic oxidation reaction whil maintaining an essentially constant reaction temperature and thereby preventing a runaway reaction. The absorbed heat of reaction from this exothermic oxidation may be employed in the process of the present invention to help maintain the molten salt in a molten state and/or to heat the gaseous reactants to reaction temperature. In the process of the present invention, the molten salt(s) is employed in an amount sufficient to maintain isothermal reaction conditions by absorbing the reaction exotherm. Typically, the molten salt(s) is employed in an amount on a weight basis of between about 5 times and about 100 times (preferably between about 5 times and about 50 times) the total weight of the reactants employed.

The nitrate salt used may be any one of the alkali or alkaline earth nitrates such as lithium, sodium, potassium, rubidium, cesium, magnesium, calcium, strontium, or barium or mixtures thereof. In addition, the nitrate salts can be used in mixtures with other salts such as chlorides, bromides, carbonates, sulfates, and phosphates. Generally, the content of the other salt(s), when present, should be restricted to less than 60 percent by weight based upon the weight of the total melt and in most cases their contents should not exceed about 25 percent of the total melt.

In a preferred embodiment of the present invention, a mixture of potassium and sodium molten nitrate salts is employed comprising between about 20 and about 80 weight percent of sodium nitrate, preferably between about 45 and about 65 weight percent of sodium nitrate based upon the total amount of sodium nitrate and potassium nitrate in the molten salt mixture. When using this mixture, it has been found in accordance with the present invention that a product molar selectivity to allyl alcohol of at least about 40 percent based upon the propylene reactant is achievable by employing a temperature of between about 325° C. and about 350° C. and a pressure of between about 250 psig and about 350 psig (most preferably about 300 psig). When using higher elevated pressures of up to 600 psig or higher, the temperature is suitably adjusted downward to provide the desired high molar selectivity of allyl alcohol product.

Mixtures of molten lithium and potassium nitrate can be suitably employed at a temperature as low as about 280° F., and hence, this temperature may be employed when using lithium nitrate mixtures. In the selection of a suitable molten nitrate salt bath temperature it is important to choose a temperature below the thermal decomposition temperature for the particular molten nitrate salt chosen. In addition, it is important to maintain a sufficient isotherm across the molten nitrate salt bath so as to avoid crust formation of the nitrate salt in the bath. Such a crust formation in the nitrate salt bath can cause localized overheating of gases trapped by the crust in the bath and an associated "runaway" oxidation reaction due to overheating of the gases in the bath. In order to maintain a bath isotherm, constant stirring of the molten nitrate salt bath is preferred. Alternatively, the molten salt can be circulated by conventional means, such as the use of internal draft tubes or external pumping loops.

The ratio of propylene to oxygen in the oxygen-containing gas in the reactor can vary over a wide range. However, in accordance with the present invention, it has now been found that enhanced selectivity of the desired allyl alcohol product is achieved by maintaining a relatively low amount of oxygen relative to the amount of propylene fed into the reactor. For example, when reacting propylene with oxygen in a molten potassium nitrate salt column at atmospheric pressure, a ratio of between about 1 and about 20 volume percent of oxygen, (e.g., about 5 volume percent oxygen to about 95 volume percent propylene), suitably provides an enhanced selectivity of allyl alcohol. When using air as the oxygen-containing gas, it is preferably employed in an amount of between about 5 and about 75 volume percent based upon the total amount of air plus propylene employed in the reaction.

Another consideration in the selection of the amount of propylene to use as a feed is its high partial pressure which in high concentrations can cause thermal cracking of propylene. Therefore, when conducting the oxidation reaction at an elevated pressure, viz 300 psig, it is generally preferred to "cut" the amount of propylene in the illustrative example to 75 volume percent and utilize an inert blanket ("diluent") gas, such as nitrogen, to provide the remaining 20 volume percent of feed gas. Preferably, the amount of propylene in the feed gas containing oxygen and an inert blanket gas is less than about 50 volume percent, more preferably between about 20 volume percent about about 35 volume percent of propylene based on the total amount of feed gas. Alternatively, the diluent gas may be comprised of mixtures of oxidation by-product gases such as acetaldehyde, methane, and carbon dioxide, generally readily obtainable from the allyl alcohol purification operations downstream of the molten salt reactor.

In the selection of the ratio of the volume of oxygen-containing gas relative to the volume of propylene employed in the reaction mixture, the range of ratios which might pose a flammability hazard should be avoided, as is well known. For example, when utilizing an air/propylene reactant mixture at atmospheric pressure, the range of below 12 volume percent of propylene based upon total air plus propylene should be avoided.

The preferred method of contacting the gaseous reactants in the presence of the molten nitrate salt is by bubbling the reactants through a bath of the molten salt, preferably in a deep bed autoclave "bubble" reactor. If the gaseous reactants are bubbled into the bottom of the bath or column containing the molten nitrate salt, the contact time of the reactants with the molten salt catalyst is equal to the "rise time" of the reactants through the bath or column. Thus, the contact time can be increased by increasing the length of the molten nitrate salt bath or column. An alternate method of contacting the gaseous reactants in the presence of the molten salt would be to pass the gaseous reactants through a reaction countercurrently to a spray or mist of the molten salt. This method provides for enhanced surface area contact of the reactants with the molten salt. Still another method of contacting the gaseous reactants with molten salt would be to inject the reactants into a circulating stream of molten salt, wherein the kinetic energy of both streams is utilized to provide intimate mixing through the application of nozzles, mixers, and other conventional equipment. This latter method is expected to be preferred in a commercial setting. These methods are only illustrative of types of reaction systems which may be employed in the practice of this disclosure. Other conventional methods of gas-liquid contact in reaction systems may also be employed.

The propylene feed gas can be passed into the molten nitrate salt-containing reactor using a separate stream (e.g. feed tube) from the stream delivering the oxygen-containing gas to the reactor. Alternatively, the reactant gases can be fed into the reactor together in a single stream. In a preferred embodiment of the present invention, two co-axially mounted feed gas tubes are employed. The co-axial mounting of the feed gas tubes has been found to reduce or minimize the back-up of molten salt into an unpressurized feed tube if pressure is temporarily lost in either (but not both) feed tube. Mixing of the gaseous reactants prior to, or at the point of, the gas(es) inlet into the reactor is desired in order to facilitate the oxidation reaction. Mixing is suitably accomplished using an impingement mixer or sparger tube.

The feed gas is preferably bubbled into the molten nitrate salt-containing reactor using a sparger. If used, the sparger is preferably positioned in the molten nitrate salt to a sparger exit port depth of between about 2 and about 1000 centimeters, preferably between about 10 and about 200 centimeters, depending upon the size of the reactor utilized and the overall depth of the molten salt in the reactor. Alternatively, the gas can be fed directly into the bottom of the reactor by a feed tube.

The process can be run in a batchwise or continuous operation, the latter being preferred. The order of introduction of the reactants is determined by the operator based on what is most safe and practical under prevalent conditions. Generally, the desirability of avoiding flammable gas mixtures throughout the reaction and subsequent product separation systems will dictate the desired procedures.

The process can be carried out by feeding a mixture of propylene, inert gas, and oxygen into a reaction vessel containing molten nitrate salt. The reaction vessel can be glass, glass-lined metal, or made of titanium. For example, a glass-lined stainless steel autoclave can be used, although, even better from a commercial point of view, is an unlined type 316 stainless steel autoclave (as defined by the American Iron and Steel Institute). A tubular reactor made of similar materials can also be used together with multi-point injection to maintain a particular ratio of reactants. Other specialized materials may be economically preferred to minimize corrosion and contamination of the molten salt and products, or to extend the useful life of the reaction system.

Some form of agitation of the molten salt(s)/feed gas mixture is preferred to avoid a static system and insure the homogeneity of the molten salt, agitation helps prevent crust formation of the salt(s) at the head gas/salt interface in the reactor. However, excessive backmixing and reactor holdup time leads to undesirable overoxidation. The proper amount of mixing can be accomplished by using a mechanically stirred autoclave, a multi-point injection system, or a continuous process, e.g., with a loop reactor wherein the reactants are force circulated through the system. Sparging alone can also be used and is sufficient in certain cases. In the subject process, it is found that increased rates of reaction are obtained by good gas-liquid contact provided by agitation of the molten salt/gas mixture without excessive backmixing of the reactant gases.

The process of the present invention is suitably carried out at atmospheric, subatmospheric or superatmospheric pressure. Preferably, the process is effected at superatmospheric pressures not exceeding 100 atmospheres, preferably between about 250 psig and about 600 psig, more preferably between about 100 psig and about 400 psig. The process is suitably effected at a temperature of between about 135° C. and about 600° C., preferably between about 135° C. and about 350° C.

It is to be understood that by-products are also produced during the reaction. For example, some dehydrogenation of the feed is also effected, particularly at higher temperatures within the hereinabove noted temperature range, and therefore, the reaction conditions are generally controlled to minimize such production. The separation of the resulting by-products in order to recover the desired product may be effected by a wide variety of well-known procedures such as: absorption in water followed by fractional distillation, absorption, and condensation.

The following examples are intended to illustrate, but in not way limit the scope of, the present invention.

EXAMPLE 1

Preparation of Allyl Alcohol in High Molar Selectivity

A four liter stainless steel autoclave reactor rated for pressures up to 5,000 psi at 250° C. was charged with 3,900 g of sodium nitrate and 2,600 g of potassium nitrate. This salt mixture was melted and brought up to 334° C. by use of an external resistance heater. Propylene at the rate of 1400 cc/min (STP) was sparged into the melt through the inner tube of a set of co-axial feed tubes. An oxygen and nitrogen mixture consisting of 130 cc/min of oxygen and 2480 cc/min of nitrogen was sparged in through the outer tube. The two feed gas streams mixed inside the porous metal sparger fitted to the end of the co-axial feed tubes and immediately entered the molten salt. The depth of the sparger element into the salt was 52 cm. The gases were brought up to 300 psig pressure using a backpressure regulator. The gases flowed into and out of the reactor in a continuous manner such that the contact time with the molten salt amounted to only a few seconds. The gases exiting the molten salt were quenched to a temperature below 200° C. by a cooling coil mounted in the head space of the reactor. The gas exiting the reactor passed through an ice water trap for easily condensible substances and through a gas sample cylinder ("sample bomb") in line after the trap. After 30 minutes of operation, the reactor off gases were sampled, the reaction was stopped by stopping the flow of the reactant feed gases, and the trap contents were collected. The gas sample and the trap sample were analyzed by gas chromatography methods. The propylene per pass conversion was determined to be 2 percent, the selectivity to allyl alcohol was found to be 48 percent based upon the propylene reactant, and the selectivity to propylene oxide was found to be 5.5 percent.

EXAMPLE 2

Preparation of Allyl Alcohol in Lower Molar Selectivity

The oxidation of propylene was carried out in the exact same manner as in EXAMPLE 1 except that the molten salt temperature was raised to 360° C. instead of 334° C. in EXAMPLE 1 above. The propylene conversion was found to be 5.1 percent, the selectivity to allyl alcohol was found to be 3.7 percent and the selectivity to propylene oxide was found to be 42.3 percent. The major other products formed were acetaldehyde at 22 percent selectivity and carbon dioxide at 18 percent selectivity.

EXAMPLE 3

Preparation of Allyl Alcohol in Lower Molar Selectivity

The oxidation of propylene was conducted in the same manner as in EXAMPLE 1 at 300 psig total pressure with a total gas flow of about 4000 cc/min, but with the exception that the propylene flow was increased to about 2000 cc/min, the oxygen flow was increased to 205 cc/min, and the nitrogen flow was decreased to 1790 cc/min. The salt temperature was also lowered to 310° C. The results from this experiment showed a propylene per pass conversion of 0.5 percent, a selectivity to allyl alcohol of 15 percent, and a selectivity to propylene oxide of 13 percent.

EXAMPLE 4

Preparation of Allyl Alcohol in Lower Molar Selectivity

When the same conditions as in EXAMPLE 3 were tried except at 355° C., the propylene per pass conversion was 4.1 percent, the selectivity to allyl alcohol was 3.3 percent, and the selectivity to propylene oxide was 43.5 percent.

EXAMPLE 3 at 310° C. and EXAMPLE 4 at 355° C. illustrate processes which provide allyl alcohol selectivities of 15 and 4 percent, respectively. This illustrates the effect of temperature upon the allyl alcohol selectivity. Under otherwise similar conditions, the selectivity to allyl alcohol is generally higher at lower temperatures or has an optimum temperature for allyl alcohol production that is much lower than the optimum temperature for production of propylene oxide.

What is claimed is:

1. A process for producing allyl alcohol by reacting propylene with an oxygen-containing gas in the presence of at least one molten nitrate salt catalyst under reaction conditions which include a temperature of between about 135° C. and about 600° C. and a superatmospheric reaction pressure not exceeding 100 atmospheres.

2. The process of claim 1 wherein said molten nitrate salt is selected from the group consisting of sodium, potassium, lithium, cesium, magnesium, and calcium molten nitrate salts, and wherein the molten salt is present in an amount sufficient to maintain isothermal reaction conditions by absorbing any reaction exotherm.

3. A process for producing allyl alcohol from propylene or mixtures of propylene and propane, which comprises bubbling an oxygen-containing gas and said propylene or mixture through a bath of at least one molten nitrate salt catalyst under reaction conditions which include a temperature of between about 135° C. and about 600° C. and a superatmospheric pressure not exceeding 100 atmospheres.

4. The method of claim 3 wherein said oxygen-containing gas is fed into said bath by means of a first tube and wherein said propylene or mixtures of propylene and propane is fed into said bath by means of a second tube, and wherein said bath is in a bubble reactor.

5. The method of claim 4 wherein said first tube and said second tube are co-axially mounted with respect to each other.

6. The method of claim 3 wherein said molten salt is selected from the group consisting of sodium, potassium, lithium, cesium, magnesium, and calcium molten nitrate salts.

7. A process for producing allyl alcohol by reacting propylene with an oxygen-containing gas in the presence of a catalyst, said catalyst consisting essentially of a mixture of sodium nitrate and potassium nitrate containing between about 20 weight percent and about 80 weight percent of sodium nitrate based upon the total amount of sodium nitrate and potassium nitrate in said mixture, under reaction conditions which include a reaction temperature of between about 275° C. and about 350° C. and a reaction pressure of between about 100 psig and about 400 psig.

8. The process of claim 7 wherein said propylene is present in an amount of less than about 50 volume percent based upon the total amount of said propylene and said oxygen-containing gas.

9. The process of claim 8 wherein said propylene is present in amount of between about 20 and about 35 volume percent based upon the total amount of said propylene and said oxygen-containing gas.

10. The process of claim 7 wherein said oxygen-containing gas is oxygen.

11. The process of claim 10 wherein said oxygen is employed in an amount of between about 1 and about 20 volume percent based on the total amount of said oxygen plus said propylene.

12. A process for producing allyl alcohol by reacting propylene with an oxygen-containing gas in the presence of a catalyst, said catalyst consisting essentially of a mixture of sodium nitrate, potassium nitrate and lithium nitrate, containing between about 10 weight percent and about 30 weight percent of lithium nitrate and between about 15 weight percent and about 75 weight percent of sodium nitrate based upon the total amount of said mixture, under reaction conditions which include a reaction temperature of between about 200° C. and about 350° C. and a reaction pressure of between about 100 psig and about 400 psig.

13. The process of claim 12 wherein said propylene is present in an amount of less than about 50 volume percent based upon the total amount of said propylene and said oxygen-containing gas.

14. The process of claim 12 wherein said propylene is present in amount of between about 20 and about 35 volume percent based upon the total amount of said propylene and said oxygen-containing gas.

15. The process of claim 12 wherein said oxygen-containing gas is oxygen.

16. The process of claim 15 wherein said oxygen is employed in an amount of between about 1 and about 20 volume percent based upon the total amount of said oxygen plus said propylene.

* * * * *